(12) United States Patent
Chung et al.

(10) Patent No.: US 8,367,885 B2
(45) Date of Patent: Feb. 5, 2013

(54) METHOD OF PREPARING MULTICOMPONENT BISMUTH MOLYBDATE CATALYSTS WITH CONTROLLING PH AND A METHOD OF PREPARING 1,3-BUTADIENE USING THEREOF

(75) Inventors: Young Min Chung, Daejeon (KR); Seong Jun Lee, Daejeon (KR); Tae Jin Kim, Daejeon (KR); Seung Hoon Oh, Seoul (KR); Yong Seung Kim, Daejeon (KR); In Kyu Song, Seoul (KR); Hee Soo Kim, Seoul (KR); Ji Chul Jung, Seoul (KR); Ho Won Lee, Seoul (KR)

(73) Assignees: SK Innovation Co., Ltd, Seoul (KR); SK Global Chemical Co., Ltd., Seoul (KR)

( * ) Notice: Subject to any disclaimer, the term of this patent is extended or adjusted under 35 U.S.C. 154(b) by 500 days.

(21) Appl. No.: 12/451,437

(22) PCT Filed: May 8, 2008

(86) PCT No.: PCT/KR2008/002586
§ 371 (c)(1),
(2), (4) Date: Nov. 9, 2009

(87) PCT Pub. No.: WO2008/147055
PCT Pub. Date: Dec. 4, 2008

(65) Prior Publication Data
US 2010/0125161 A1    May 20, 2010

(30) Foreign Application Priority Data
May 30, 2007   (KR) ........................ 10-2007-0052671

(51) Int. Cl.
*C07C 5/48*    (2006.01)

(52) U.S. Cl. ........ 585/626; 585/616; 585/617; 585/621; 585/624; 502/305; 502/311

(58) Field of Classification Search .................. 585/601, 585/616, 617, 621, 624, 626; 502/305, 311
See application file for complete search history.

(56) References Cited

U.S. PATENT DOCUMENTS 3,414,631 A * 12/1968 Grasselli et al. .............. 585/622
3,966,823 A * 6/1976 Takenaka et al. .............. 568/479
(Continued)

OTHER PUBLICATIONS

Soares, et al., "Synergy Effects Between β and γ Phases of Bismuth Molybdates in the Selective Catalytic Oxidation of 1-Butene" in Applied Catalysis A: General 253 (2003), 191-200—2003, month unknown.*

(Continued)

*Primary Examiner* — In Suk Bullock
*Assistant Examiner* — Bradley Etherton
(74) *Attorney, Agent, or Firm* — Abelman, Frayne & Schwab

(57) ABSTRACT

This invention relates to a method of preparing a multicomponent bismuth molybdate catalyst by changing the pH of a coprecipitation solution upon coprecipitation and a method of preparing 1,3-butadiene using the catalyst. The multicomponent bismuth molybdate catalyst, coprecipitated using a solution having an adjusted pH, the preparation method thereof, and the method of preparing 1,3-butadiene through oxidative dehydrogenation using a C4 mixture including n-butene and n-butane as a reactant are provided. The C4 raffinate, containing many impurities, is directly used as a reactant without an additional process for separating n-butane or extracting n-butene, thus obtaining 1,3-butadiene at high yield. The activity of the multicomponent bismuth molybdate catalyst can be simply increased through precise pH adjustment upon coprecipitation, which is not disclosed in the conventional techniques. This method can be applied to the increase in the activity of multicomponent bismuth molybdate catalysts reported in the art.

7 Claims, 2 Drawing Sheets

U.S. PATENT DOCUMENTS 3,972,954 A * 8/1976 Bertus ............................ 585/622
4,547,615 A * 10/1985 Yamamoto .................... 585/621

OTHER PUBLICATIONS

Lide, CRC Handbook of Chemistry and Physics, 92nd ed., 2012 Internet version, D. R. Lide, ed.—accessed Mar. 28, 2012.*

W. Ronald Cares and Joe W. Hightower, "Ferrite Spinels as Catalysts in the Oxidative Dehydrogenation of Butenes", Journal of Catalysis 23, 193-203 (1971), Department of Chemical Engineering, Rice University, Houston, Texas.

Michael A. Gibson and Joe W. Hightower, "Oxidative Dehydrogenation of Butenes over Magnesium Ferrite, Kinetic and Mechanistic Studies", Journal of Catalysis 41, 420-430 (1976), Department of Chemical Engineering, Rice University, Houston, Texas.

J.A. Toledo et al., "Oxidative dehydrogenation of 1-butene to butadiene on $\alpha$-Fe2O3/ZnAl2O4 and ZnFexAl2-xO4 catalysts", Catalysis Letters 30 (1995) 279-288, Instituto Mexicano del Petroleo, SGIDTTI Eje Central L. Cardenas No. 152, A.P. 14-805, CP07730, Mexico D.F., Mexico.

Yu M. Bakshi et al., Catalytic Properties of System SnO2:Sb2O4 in the Oxidative Dehydrogenation of n-Butenes to Butadiene, L Ya Karpov Physicochemical Institute, Jan. 1966, 177-185.

A.C.A.M. Bleijenberg et al., Catalytic Oxidation of 1-Butene over Bismuth Molybdate Catalysts, Journal of Catalysis , 581-586, (1965), Department of Inorganic Chemistry, Technological University, Eindhoven, The Netherlands.

Harold H. Kung and Mayfair C. Kung, "Selective Oxidative Dehydrogenation of Butenes on Ferrite Catalysts", Advances in Catalysis, vol. 33, 1985, 159-198, Chemical Engineering Department and the Ipatieff Catalytic Laboratory, Northwestern University, Evanston, Illinois.

* cited by examiner

METHOD OF PREPARING MULTICOMPONENT BISMUTH MOLYBDATE CATALYSTS WITH CONTROLLING PH AND A METHOD OF PREPARING 1,3-BUTADIENE USING THEREOF

TECHNICAL FIELD

The present invention relates to a method of preparing a multicomponent bismuth molybdate catalyst through changes in the pH of a coprecipitation solution upon coprecipitation and a method of preparing 1,3-butadiene using the catalyst, and more particularly, to a method of preparing a multicomponent bismuth molybdate catalyst through coprecipitation using a solution having an adjusted pH, and furthermore, to a method of preparing high value-added 1,3-butadiene from an inexpensive C4 mixture including n-butene and n-butane, without an additional process for separating n-butane or extracting n-butene, in the presence of the above catalyst.

BACKGROUND ART

Generally, methods of obtaining 1,3-butadiene, the demand for which is gradually increasing in petrochemical markets, include naphtha cracking, direct dehydrogenation of n-butene, and oxidative dehydrogenation of n-butene. However, the naphtha cracking process, which is responsible for 90% of the 1,3-butadiene that is supplied, entails high energy consumption due to high reaction temperatures. As well, because this process is not a single process for producing only 1,3-butadiene, investment in and management of a naphtha cracker are difficult to optimize in order to meet the production demand of 1,3-butadiene. That is, to meet the increased butadiene demand through the above process, more novel naphtha crackers need to be established, and accordingly, raffinate components other than 1,3-butadiene are produced in surplus. In addition, the direct dehydrogenation of n-butene, which is an endothermic reaction, requires high-temperature and low-pressure conditions to produce 1,3-butadiene at high yield, and is thermodynamically disadvantageous, and is thus unsuitable for commercially producing 1,3-butadiene [M. A. Chaar, D. Patel, H. H. Kung, J. Catal., vol. 109, pp. 463 (1988)/E. A. Mamedov, V. C. Corberan, Appl. Cata. A, vol. 127, pp. 1 (1995)/L. M. Madeira, M. F. Portela, Catal. Rev., vol. 44, pp. 247 (2002)].

In addition, the oxidative dehydrogenation of n-butene is a reaction between n-butene and oxygen that produces 1,3-butadiene and water. This reaction is thermodynamically advantageous because water, which is stable, is produced as a product, and is also commercially advantageous because 1,3-butadiene may be obtained at high yield even at decreased reaction temperatures, without the need to additionally apply heat, thanks to exothermic properties. Further, this process additionally produces steam and is thus advantageous in terms of energy reduction. Hence, the oxidative dehydrogenation of n-butene for the production of 1,3-butadiene is considered to be an effective alternative that enables the production of 1,3-butadiene through a single process. In particular, when a C4 raffinate-3 or C4 mixture including impurities, such as n-butane, is directly used as a source of n-butene without an additional separation process, an advantage of adding high value to surplus C4 raffinate components may be realized. Specifically, the C4 raffinate-3 mixture, which is the reactant used in the present invention, is an inexpensive C4 raffinate remaining after the separation of useful compounds from a C4 mixture produced through naphtha cracking. More specifically, a first mixture remaining after extracting 1,3-butadiene from a C4 mixture produced through naphtha cracking is called raffinate-1, a second mixture remaining after extracting isobutylene from the raffinate-1 is called raffinate-2, and a third mixture remaining after extracting 1-butene from the raffinate-2 is called raffinate-3. Therefore, the C4 raffinate-3 or C4 mixture is composed mainly of 2-butene (trans-2-butene and cis-2-butene), n-butane, and 1-butene.

As mentioned above, according to the oxidative dehydrogenation of n-butene (1, butane, trans-2-butene, cis-2-butene), n-butene reacts with oxygen, thus producing 1,3-butadiene and water. Although the oxidative dehydrogenation of n-butene is an effective alternative that produces 1,3-butadiene through a single process, this reaction is supposed to cause many side-reactions, including complete oxidation, etc., due to the use of oxygen as the reactant. Thus, the development of catalysts that maximally inhibit such side-reactions and have high selectivity for 1,3-butadiene is of utmost importance. The catalysts for use in the oxidative dehydrogenation of n-butene, known to date, include ferrite-based catalysts [R. J. Rennard, W. L. Kehl, J. Catal., vol. 21, pp. 282 (1971)/W. R. Cares, J. W. Hightower, J. Catal., vol. 23, pp. 193 (1971)/M. A. Gibson, J. W. Hightower, J. Catal., vol. 41, pp. 420 (1976)/H. H. Kung, M. C. Kung, Adv. Catal., vol. 33, pp. 159 (1985)/J. A. Toledo, M. A. Valenzuela, H. Armendariz, G. Aguilar-Rios, B. Zapzta, A. Montoya, N. Nava, P. Salas, I. Schifter, Catal. Lett., vol. 30, pp. 279 (1995)], tin-based catalysts [Y. M. Bakshi, R. N. Gur'yanova, A. N. Mal'yan, A. I. Gel'bshtein, Petroleum Chemistry U.S.S.R., vol. 7, pp. 177 (1967)], bismuth molybdate-based catalysts [A. C. A. M. Bleijenberg, B. C. Lippens, G. C. A. Schuit, J. Catal., vol. 4, pp. 581 (1965)/Ph. A. Batist, B. C. Lippens, G. C. A. Schuit, J. Catal., vol. 5, pp. 55 (1966)/M. W. J. Wolfs, Ph. A. Batist, J. Catal., vol. 32, pp. 25 (1974)/W. J. Linn, A. W. Sleight, J. Catal., vol. 41, pp. 134 (1976)/W. Ueda, K. Asakawa, C.-L. Chen, Y. Moro-oka, T. Ikawa, J. Catal., vol. 101, pp. 360 (1986)/Y. Moro-oka, W. Ueda, Adv. Catal., vol. 40, pp. 233 (1994)/R. K. Grasselli, Handbook of Heterogeneous Catalysis, vol. 5, pp. 2302 (1997)].

Among these catalysts, the bismuth molybdate-based catalyst includes bismuth molybdate catalysts composed exclusively of bismuth and molybdenum oxide and multicomponent bismuth molybdate catalysts further comprising various metal components. Pure bismuth molybdate is present in various phases, and, in particular, three phases including α-bismuth molybdate ($Bi_2Mo_3O_{12}$), β-bismuth molybdate ($Bi_2Mo_2O_9$) and γ-bismuth molybdate ($Bi_2MoO_6$) are known to be useful as catalysts [B. Grzybowska, J. Haber, J. Komorek, J. Catal., vol. 25, pp. 25 (1972)/A. P. V. Soares, L. K. Kimitrov, M. C. A. Oliveira, L. Hilaire, M. F. Portela, R. K. Grasselli, Appl. Catal. A, vol. 253, pp. 191 (2003)]. However, a process of preparing 1,3-butadiene through oxidative dehydrogenation of n-butene in the presence of a pure bismuth molybdate catalyst having a single phase is unsuitable for commercialization, attributable to the production of 1,3-butadiene at low yield [Y. Moro-oka, W. Ueda, Adv. Catal., vol. 40, pp. 233 (1994)]. As an alternative thereto, in order to increase activity for the oxidative dehydrogenation of n-butene, attempts to prepare multicomponent bismuth molybdate catalysts comprising not only bismuth and molybdate but also various metal components have been made [M. W. J. Wolfs, Ph. A. Batist, J. Catal., vol. 32, pp. 25 (1974)/S. Takenaka, A. Iwamoto, U.S. Pat. No. 3,764,632 (1973)].

Some patents and literature have reported multicomponent bismuth molybdate catalysts for the oxidative dehydrogenation of n-butene. Specifically, many reports have been made of the oxidative dehydrogenation of 1-butene at 520° C. using a mixed oxide catalyst composed of nickel, cesium, bismuth, and molybdenum, resulting in 1,3-butadiene at a yield of 69% [M. W. J. Wolfs, Ph. A. Batist, J. Catal., vol. 32, pp. 25 (1974)], of the oxidative dehydrogenation of a C4-mixture including n-butane and n-butene at 470° C. using a mixed oxide catalyst composed of cobalt, iron, bismuth, magnesium, potassium, and molybdenum, resulting in 1,3-butadiene at a maximum yield of 62% [S. Takenaka, H. Shimizu, A. Iwamoto, Y. Kuroda, U.S. Pat. No. 3,998,867 (1976)], and of the oxidative dehydrogenation of 1-butene at 320° C. using a mixed oxide catalyst composed of nickel, cobalt, iron, bismuth, phosphorus, potassium, and molybdenum, resulting in 1,3-butadiene at a maximum yield of 96% [S. Takenaka, A. Iwamoto, U.S. Pat. No. 3,764,632 (1973)].

In this way, when the multicomponent bismuth molybdate catalyst disclosed in the above literature is used, 1,3-butadiene may be obtained at a very high yield, but limitations are imposed on increasing the catalytic activity because the catalyst can be prepared only through the addition of simple metal components and changes in the ratio thereof. Further, the catalytic activity is drastically decreased over the reaction time, and thus, to increase the catalytic activity, additional metal components must be continuously added, and thus the catalyst has a very complicated composition and it is difficult to ensure reproducibility. In the above conventional techniques, only pure n-butene (1-butene or 2-butene) is used as the reactant, or otherwise, even if a mixture of n-butane and n-butene serves as the reactant, a C4 mixture including n-butane in a small amount less than 10 wt % is used. Accordingly, in the case where the amount of n-butane is increased, the yield of 1,3-butadiene is expected to decrease. In order to use a C4 mixture including a large amount of n-butene as the reactant in an actual petrochemical process, a process of separating n-butene from the other C4 mixture components should be essentially performed, remarkably decreasing economic efficiency. As a typical example, in a commercial process using a ferrite catalyst, a C4 mixture in which the amount of n-butane is maintained as low as less than 5 wt % is used as the reactant.

As mentioned above, the literature and patents regarding the catalyst and process for preparing 1,3-butadiene through the oxidative dehydrogenation of n-butene are characterized in that pure 1-butene, 2-butene or a mixture thereof is used as the reactant, or otherwise, a C4 mixture including a very large amount of n-butene is used as the reactant, and further, multicomponent metal oxide having a very complicated composition, resulting from the addition of simple metal components and changes in the ratio thereof, is used as the catalyst. However, cases in which 1,3-butadiene is prepared from a C4 raffinate, including C4 raffinate-3 or a C4 mixture having a high concentration of n-butane, in the presence of a multicomponent bismuth molybdate catalyst comprising relatively simple metal components prepared through coprecipitation using a coprecipitation solution, the pH of which is adjusted, have not yet been reported.

DISCLOSURE

Technical Problem

Therefore, as a result of continuous studies to overcome the limitations of the conventional techniques, the present inventors have discovered that multicomponent bismuth molybdate may be prepared through coprecipitation using a coprecipitation solution having an adjusted pH, whereby it is possible to prepare a multicomponent bismuth molybdate catalyst composed of simple metal components exhibiting high activity for the oxidative dehydrogenation of n-butene, even without the addition of other complicated metal components or changes in the ratio thereof, and in particular, 1,3-butadiene may be produced through oxidative dehydrogenation using an inexpensive C4 mixture including n-butane in a large amount and n-butene, as a reactant, in the presence of the above catalyst, even without an additional separation process, thus completing the present invention.

Accordingly, the present invention provides a method of preparing a multicomponent bismuth molybdate catalyst for the production of 1,3-butadiene through coprecipitation using a coprecipitation solution having an adjusted pH. In addition, the present invention provides a method of producing 1,3-butadiene through oxidative dehydrogenation directly using a C4 mixture as a reactant without an additional separation process in the presence of the catalyst prepared by the above method.

Technical Solution

According to the present invention, a method of preparing a multicomponent bismuth molybdate catalyst for use in preparation of 1,3-butadiene may comprise a) preparing a first solution including a divalent cation metal component precursor, a trivalent cation metal component precursor, and a bismuth precursor; b) preparing a second solution in which a molybdenum precursor is dissolved; c) adding the first solution to the second solution, performing coprecipitation to obtain a coprecipitation solution, and adding a 1~3 M alkaline solution in droplets to the coprecipitation solution so that the pH of the coprecipitation solution is adjusted to 6~8; and d) stirring the coprecipitation solution having an adjusted pH for 1~2 hours, and removing water therefrom, thus obtaining a solid component; and e) drying the solid component at 20~300° C., and then performing thermal treatment at 400~600° C.

In addition, a method of preparing 1,3-butadiene may comprise a) packing the bismuth molybdate catalyst prepared using the above method in a fixed bed of a reactor; b) performing oxidative dehydrogenation while continuously passing a C4 mixture including n-butene, air, and steam, as reactants, through the catalyst bed of the reactor; and c) obtaining 1,3-butadiene.

Advantageous Effects

According to the present invention, a multicomponent bismuth molybdate catalyst for use in the production of 1,3-butadiene, which is advantageous because it shows high activity for the oxidative dehydrogenation of n-butene, can be obtained through the adjustment of the pH of a coprecipitation solution without the addition of metal components or changes in the ratio thereof. When the multicomponent bismuth molybdate catalyst of the present invention is used, 1,3-butadiene can be produced through oxidative dehydrogenation directly using a C4 mixture composed mainly of n-butane and n-butene as a reactant, even though the C4 mixture including a large amount of n-butane is not subjected to additional n-butane separation. Further, it is expected that the method of preparing the multicomponent bismuth molybdate catalyst through adjustment of the pH of the coprecipitation solution according to the present invention can be applied to the preparation of multicomponent bismuth molybdate catalysts which are typical in the art, so that the activity of catalysts disclosed in some conventional literature and patents can be further increased.

In the present invention, the C4 mixture or C4 raffinate-3, which is of little usefulness in the petrochemical industry, can be directly utilized for the preparation of 1,3-butadiene, thereby ensuring a single process for producing 1,3-butadiene and adding value to the inexpensive C4 raffinate. Moreover, a single process for producing 1,3-butadiene is ensured, thereby realizing the optimized production for the increased 1,3-butadiene demand.

BEST MODE

Figure 1:
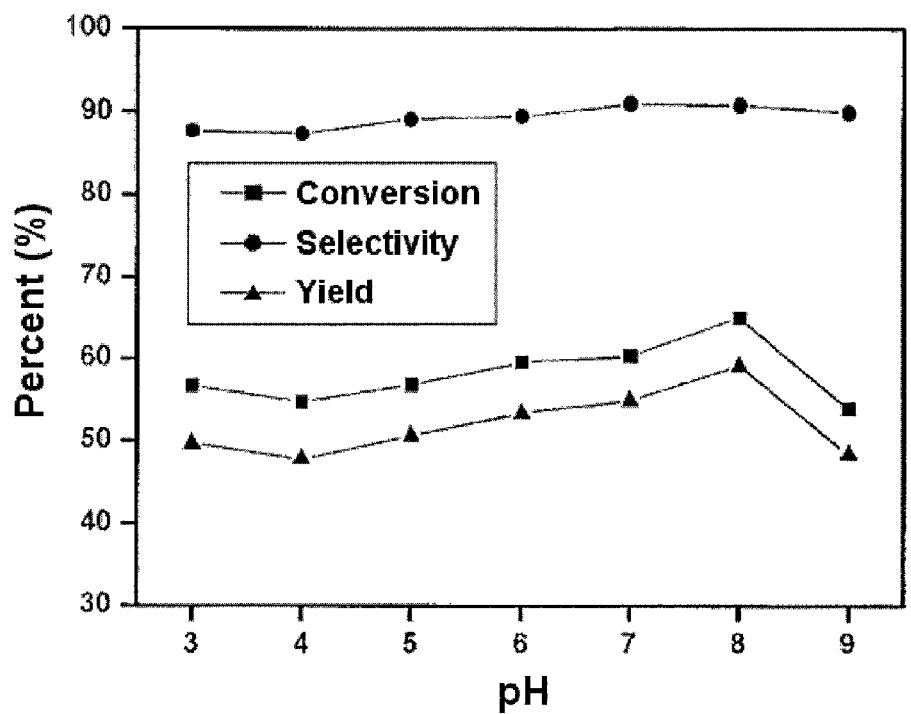
FIG. 1 is a graph showing the changes in reaction activity of seven kinds of multicomponent bismuth molybdate catalysts depending on the pH of a coprecipitation solution in the course of coprecipitation, according to an embodiment of the present invention.

Hereinafter, a detailed description will be given of the present invention. As mentioned above, the present invention is directed to methods of preparing a multicomponent bismuth molybdate catalyst suitable for the oxidative dehydrogenation of n-butene, having a simpler composition compared to conventional techniques, through coprecipitation using a solution having an adjusted pH, and of preparing 1,3-butadiene through oxidative dehydrogenation of n-butene using the prepared catalyst, in which a C4 mixture which is not subjected to an additional n-butane separation process is used as a reactant.

Specifically, in the present invention, the C4 mixture indicates an inexpensive C4 raffinate composed mainly of n-butane and n-butene remaining after separating useful compounds from a C4 mixture produced through naphtha cracking. Typically, a first mixture remaining after extracting 1,3-butadiene from the C4 mixture is called raffinate-1, a second mixture remaining after extracting isobutylene from the raffinate-1 is called raffinate-2, and a third mixture remaining after extracting 1-butene from the raffinate-2 is called raffinate-3. Thus, the C4 mixture serving as the reactant in the present invention is a C4 raffinate-3 or C4 mixture, which is composed mainly of 2-butene (trans-2-butene and cis-2-butene), n-butane, and 1-butene.

The catalyst of the present invention for use in the production of 1,3-butadiene at high yield through the oxidative dehydrogenation of n-butene is a multicomponent bismuth molybdate catalyst prepared through coprecipitation using a coprecipitation solution having an adjusted pH.

The catalytic activity of the multicomponent bismuth molybdate catalyst varies depending on the number of metal components and changes in the ratio thereof. In the present invention, a multicomponent bismuth molybdate catalyst, which is relatively simple in that it is composed of four metal components and shows high activity for the oxidative dehydrogenation of n-butene, is prepared through precise adjustment of the pH of the coprecipitation solution, without the addition of metal components or changes in the ratio thereof, as in the conventional techniques.

The multicomponent bismuth molybdate catalyst composed of four metal components includes a divalent cation metal component (e.g., Ca, Mg, Fe, Mn, Sr, Ni), a trivalent cation metal component (e.g., Fe, Al), bismuth, and molybdenum. The divalent and trivalent cation metal components include metals, which are typically and mainly used in the art. In the present invention, nickel is used as a divalent cation metal, and iron is used as a trivalent cation metal. Further, as metal precursors for the preparation of the multicomponent bismuth molybdate catalyst, any metal precursor may be used as long as it is typically known in the art. In the present invention, the nickel precursor is exemplified by nickel nitrate, the iron precursor is exemplified by iron nitrate, the bismuth precursor is exemplified by bismuth nitrate, and the molybdenum precursor is exemplified by ammonium molybdate. Also, the ratio of the precursors may be variously changed to prepare multicomponent bismuth molybdate catalysts. In the present invention, in order to increase catalytic activity through pH adjustment upon coprecipitation, the molar ratio of nickel precursor to iron precursor to bismuth precursor to molybdenum precursor is preferably set to 1~10:1~5:1:5~20, and more preferably to 8~9:2.5~3.5:1:11~12.

The nickel, iron and bismuth precursors are dissolved together in distilled water, and also, the molybdenum precursor is separately dissolved in distilled water, after which the precursor solutions are mixed together. As such, depending on the type of precursor, an acid solution (e.g., nitric acid) may be added to increase the solubility thereof. When the precursors are completely dissolved, the precursor solution containing nickel, iron and bismuth is introduced into the precursor solution containing molybdenum. In this case, in order to uniformly adjust and maintain the pH of the coprecipitation solution, a 1~3 M alkaline solution may be added together at a predetermined rate. The alkaline solution that is added is not particularly limited, and includes, for example, sodium hydroxide, potassium hydroxide, and ammonia solutions. In an embodiment of the present invention, an ammonia solution is used. If the concentration of the alkaline solution is lower than 1 M or higher than 3 M, the formation of a phase showing the catalytic activity is problematic, and unnecessary phases other than a desired phase may be formed together, thereby deteriorating the catalytic activity.

The addition rate of the precursor solution containing bismuth and the addition rate of the alkaline solution, such as ammonia solution, are controlled, so that the pH of the coprecipitation solution upon coprecipitation is uniformly maintained at 6~8. The solution coprecipitated at a predetermined pH is stirred for 0.5~5 hours, and preferably 1~2 hours, for sufficient coprecipitation. Water and other liquid components are removed from the stirred solution using a vacuum concentrator or a centrifuge, thus obtaining a solid sample. The solid sample thus obtained is dried at 20~300° C., and preferably 150~200° C. for 12~24 hours. The solid catalyst thus produced is placed in an electrical furnace, and then thermal treatment is performed at a temperature of 300~800° C., preferably 400~600° C., and more preferably 450~500° C., thereby preparing a multicomponent bismuth molybdate catalyst.

According to the present invention, the technique for preparing the multicomponent bismuth molybdate catalyst through the adjustment of the pH of the coprecipitation solution upon coprecipitation is not limited to the preparation of the multicomponent bismuth molybdate catalyst composed of four metal components, but may be applied to the preparation of multicomponent bismuth molybdate mixed oxide catalysts composed of three or more metal components in addition to bismuth and molybdenum.

According to the present invention, in the presence of the multicomponent bismuth molybdate catalyst, the reaction occurs in a manner such that n-butene, acting as the reactant, is adsorbed on the catalyst, lattice oxygen of the catalyst reacts with two hydrogens of n-butene which are adsorbed, thus producing 1,3-butadiene and water, and the lattice oxygen vacancy of the catalyst is occupied with molecular oxygen, which is the reactant. In this way, when n-butene is adsorbed on the catalyst, the site of the catalyst able to activate n-butene and the lattice oxygen properties of the catalyst influence the reaction activity. Further, because the multicomponent bismuth molybdate catalysts prepared through coprecipitation using the solution at different pH values have different catalyst phase ratios and lattice oxygen properties, the multicomponent bismuth molybdate catalysts prepared through the adjustment of the pH of the coprecipitation solution exhibit different activities.

According to the embodiment of the present invention, even when the multicomponent bismuth molybdate catalysts are composed of the same metal components, the catalytic activity thereof is seen to vary depending on the pH of the coprecipitation solution (FIG. 1). Specifically, it is possible to prepare multicomponent bismuth molybdate catalysts showing high activity for the present reaction even though they include relatively simple metal components, merely through the adjustment of the pH of the coprecipitation solution without the addition of metal components or changes in the ratio thereof.

Hence, the catalyst for the production of 1,3-butadiene according to the present invention is a multicomponent bismuth molybdate catalyst prepared using the coprecipitation solution having a predetermined pH. The multicomponent bismuth molybdate catalyst prepared at a predetermined pH is obtained using the coprecipitation solution, the pH of which is set to 6~8, in consideration of the catalytic activity.

In addition, the present invention provides a method of preparing 1,3-butadiene through oxidative dehydrogenation using a C4 mixture or C4 raffinate-3 including a large amount of n-butane, which is not subjected to an additional n-butane separation process, as a source of n-butene, in the presence of the multicomponent bismuth molybdate catalyst prepared using the coprecipitation solution having a predetermined pH.

In the experimental example of the present invention, a straight type Pyrex reactor for a catalytic reaction is mounted in an electrical furnace so that the reaction temperature is maintained uniform, and the reaction is conducted while the reactant is continuously passed through the catalyst bed of the reactor. The reaction temperature is set to 300~600° C., preferably 350~500° C., and more preferably 420° C. Further, the amount of catalyst is set such that GHSV (Gas Hourly Space Velocity) is 50~5000 $h^{-1}$, preferably 100~1000 $h^{-1}$, and more preferably 150~500 $h^{-1}$, based on n-butene. The volume ratio of n-butene to air to steam, which are supplied as reactants, is set to 1:0.5~10:1~50, and preferably 1:3~4:10~30. In the present invention, the amounts of C4 mixture or C4 raffinate-3, as a source of n-butene, and of air as another reactant are precisely controlled using a mass flow controller. Water in a liquid phase is evaporated while being injected using a syringe pump, so that steam is supplied into the reactor. The temperature of the portion of the reactor where water in a liquid phase is injected is maintained at 150~300° C., and preferably 180~250° C., so that water injected by the syringe pump is instantly evaporated into steam, which is then mixed with the other reactants (C4 mixture and air), after which the mixture is passed through the catalyst bed of the reactor.

Among the reactants which are reacted in the presence of the catalyst of the present invention, the C4 mixture includes 0.5~50 wt % of n-butane, 40~99 wt % of n-butene, and 0.5~10 wt % of other C4 compounds. The other C4 compounds include, for example, isobutane, cyclobutane, methylcyclopropane, and isobutene.

In the presence of the multicomponent bismuth molybdate catalyst prepared using the coprecipitation solution having a predetermined pH according to the present invention, 1,3-butadiene can be produced at high yield through the oxidative dehydrogenation of n-butene using the inexpensive C4 mixture or C4 raffinate-3 including n-butane and n-butene as the reactant. In particular, even when the C4 mixture including n-butane in a high concentration of at least 20 wt % is directly used as the reactant without an additional n-butane separation process, high conversion of n-butene and high selectivity for 1,3-butadiene may result, and the activity may be maintained for a long period of time.

Moreover, in the present invention, conventional limitations of increasing the activity of the multicomponent bismuth molybdate catalyst through the addition of metal components and the changes in the ratio thereof are overcome, and the catalytic activity is enhanced through the adjustment of the pH of the coprecipitation solution. Accordingly, the present technique is advantageous because it can be applied to the preparation of any multicomponent bismuth molybdate catalyst which is typical in the art, thereby enabling an increase in the activity thereof; and further, can be directly applied to a commercialization process without the need for an additional process for separating the reactant because 1,3-butadiene can be obtained at high yield even when the C4 mixture or C4 raffinate-3, containing many impurities, is used as the reactant.

[Mode for Invention]

A better understanding of the present invention may be obtained through the following examples, which are set forth to illustrate, but are not to be construed as the limit of the present invention.

PREPARATIVE EXAMPLE 1

Selection of Metal Precursors and Solvents for Preparation of Multicomponent Bismuth Molybdate Catalysts Nickel nitrate hexahydrate ($Ni(NO_3)_2.6H_2O$) as a nickel precursor, ferric nitrate nonahydrate ($Fe(NO_3)_3.9H_2O$) as an iron precursor, bismuth nitrate pentahydrate ($Bi(NO_3)_2.5H_2O$) as a bismuth precursor, and ammonium molybdate tetrahydrate ($(NH_4)_6Mo_7O_{24}.4H_2O$) as a molybdenum precursor were used. Bismuth nitrate pentahydrate was well dissolved in a strong acid solution, whereas the other metal precursors were well dissolved in distilled water, and thus, bismuth nitrate pentahydrate was separately dissolved using distilled water to which a nitric acid solution was added.

Preparation of Multicomponent Bismuth Molybdate Catalysts Using Coprecipitation Solution Having Predetermined pH Specifically, in order to prepare multicomponent bismuth molybdate catalysts, 7.92 g of nickel nitrate hexahydrate ($Ni(NO_3)_2.6H_2O$) and 3.66 g of ferric nitrate nonahydrate ($Fe(NO_3)_3.9H_2O$) were dissolved in distilled water (50 ml) and stirred. Separately, 1.47 g of bismuth nitrate pentahydrate ($Bi(NO_3)_2.5H_2O$) was dissolved in distilled water (15 ml) containing 3 ml of nitric acid with stirring. After the complete dissolution of bismuth, the bismuth solution was added to the solution in which nickel and iron precursors were dissolved, thus preparing an acid solution in which nickel, iron and bismuth precursors were dissolved. Further, 6.36 g of ammonium molybdate tetrahydrate ($(NH_4)_6Mo_7O_{24} \cdot 4H_2O$) was dissolved in distilled water (100 ml) and stirred, and thus the solution thereof was separately prepared. The acid solution in which nickel, iron, and bismuth precursors were dissolved was added in droplets to the molybdate solution. As such, to accurately adjust the pH, while a 3 M ammonia solution was added in droplets thereto, the acid solution and the ammonia solution were added at different rates, such that the pH of the coprecipitation solution was adjusted to 3, 4, 5, 6, 7, 8, and 9.

The mixture solution thus produced was stirred at room temperature for 1 hour using a magnetic stirrer, after which the precipitated solution was subjected to vacuum concentration or centrifugation, thus obtaining a solid sample. The solid sample thus obtained was dried at 175° C. for 24 hours. The produced solid catalyst was placed in an electrical furnace and then thermally treated at 475° C., thereby preparing multicomponent bismuth molybdate catalysts coprecipitated from the coprecipitation solution having a predetermined pH. The prepared catalysts were subjected to element analysis (ICP-AES), whereby the amounts of desired metal precursors were analyzed as being accurately coprecipitated within the error range. The results are shown in Table 1 below.

TABLE 1

Element Ratio of Catalysts (Relative Molar Ratio of Other Metal Components to Bi)

| Coprecipitation Solution, pH | Ni | Fe | Bi | Mo |
|---|---|---|---|---|
| 3 | 8.6 | 3.0 | 1.0 | 11.3 |
| 4 | 8.6 | 3.0 | 1.0 | 11.3 |
| 5 | 9.3 | 3.0 | 1.0 | 11.4 |
| 6 | 8.6 | 2.9 | 1.0 | 11.3 |
| 7 | 8.8 | 2.8 | 1.0 | 11.2 |
| 8 | 8.7 | 2.9 | 1.0 | 11.4 |
| 9 | 8.5 | 2.9 | 1.0 | 11.3 |

EXPERIMENTAL EXAMPLE 1

Oxidative Dehydrogenation of C4 Raffinate-3 or C4 Mixture in Presence of Multicomponent Bismuth Molybdate Catalyst Using the multicomponent bismuth molybdate catalysts prepared in Preparative Example 1, oxidative dehydrogenation of n-butene was conducted. As reactants, a C4 mixture, air and steam were used, and a straight type Pyrex reactor was used as a reactor. The composition of the C4 mixture serving as the reactant is shown in Table 2 below. The ratio of reactants and GHSV were set based on n-butene in the C4 mixture. The ratio of n-butene to air to steam was set to 1:3.75:15. The reaction device was designed such that steam was introduced in the form of water to the inlet of the reactor, specifically, water was directly evaporated into steam at 200° C., mixed with the other reactants, that is, the C4 mixture and air, and then introduced into the reactor. The amounts of the C4 mixture and air were controlled using a mass flow controller, and the amount of steam was controlled by adjusting the injection speed of a syringe pump containing water. The reaction temperature was maintained at 475° C. The amount of the catalyst was set so that GHSV was 475 $h^{-1}$ based on n-butene, after which the reaction was conducted. Thereafter, the reaction product was analyzed using gas chromatography. The product was composed of carbon dioxide resulting from complete oxidation, cracking by-products, and n-butane, in addition to desired 1,3-butadiene. The conversion of n-butene, the selectivity of 1,3-butadiene and the yield of 1,3-butadiene were calculated from Equations 1, 2, and 3 below.

$$\text{Conversion}(\%) = (\text{number of moles of n-butene reacted/number of moles of n-butene supplied}) \times 100 \quad \text{Equation 1}$$

$$\text{Selectivity}(\%) = (\text{number of moles of 1,3-butadiene produced/number of moles of n-butene reacted}) \times 100 \quad \text{Equation 2}$$

$$\text{Yield}(\%) = (\text{number of moles of 1,3-butadiene produced/number of moles of n-butene supplied}) \times 100 \quad \text{Equation 3}$$

TABLE 2

Composition of C4 Mixture as Reactant

| Composition | Molecular Formula | Mass % |
|---|---|---|
| Iso-butane | $C_4H_{10}$ | 0.07 |
| n-Butane | $C_4H_{10}$ | 41.57 |
| Methyl Cyclopropane | $C_4H_8$ | 0.09 |
| Trans-2-butene | $C_4H_8$ | 33.94 |
| 1-Butene | $C_4H_8$ | 7.52 |
| Isobutylene | $C_4H_8$ | 0.02 |
| Cis-2-butene | $C_4H_8$ | 16.48 |
| Cyclopropane | $C_4H_8$ | 0.29 |
| Iso-pentane | $C_5H_{12}$ | 0.02 |
| | | 100 |

The multicomponent bismuth molybdate catalysts coprecipitated from the coprecipitation solution having a predetermined pH were applied to the present reaction. The results are shown in Table 3 below.

TABLE 3

Reaction Activity of Multicomponent Bismuth Molybdate Catalysts

| Coprecipitation Solution, pH | n-Butene Conversion (%) | 1,3-Butadiene Selectivity (%) | 1,3-Butadiene Yield (%) |
|---|---|---|---|
| 3 | 56.7 | 87.7 | 49.7 |
| 4 | 54.7 | 87.4 | 47.8 |
| 5 | 56.8 | 89.1 | 50.6 |
| 6 | 59.6 | 89.5 | 53.3 |
| 7 | 60.3 | 91.0 | 54.9 |
| 8 | 65.1 | 90.8 | 59.1 |
| 9 | 53.8 | 89.9 | 48.4 |

EXPERIMENTAL EXAMPLE 2

Change in Reaction Activity of Multicomponent Bismuth Molybdate Catalyst Depending on pH of Coprecipitation Solution Upon Coprecipitation According to the catalyst preparation in Preparative Example 1 and the experiment of reaction activity in Experimental Example 1, the effects of the pH of the coprecipitation solution on the reaction activity of multicomponent bismuth molybdate are shown in FIG. 1. As the pH of the coprecipitation solution was increased, the reaction activity was observed to generally increase, the activity being the greatest at pH 8 and then decreased at pH 9. Thus, through the changes in the pH of the coprecipitation solution, the activity of the multicomponent bismuth molybdate catalyst could be seen to be controlled. This is considered to be because the prepared catalysts have different phases and ratios thereof at respective pH values, and thus the catalytic activity varies depending on the changes in the properties of the catalyst itself.

EXPERIMENTAL EXAMPLE 3

Oxidative Dehydrogenation of n-Butene Depending on Reaction Time

Figure 2:
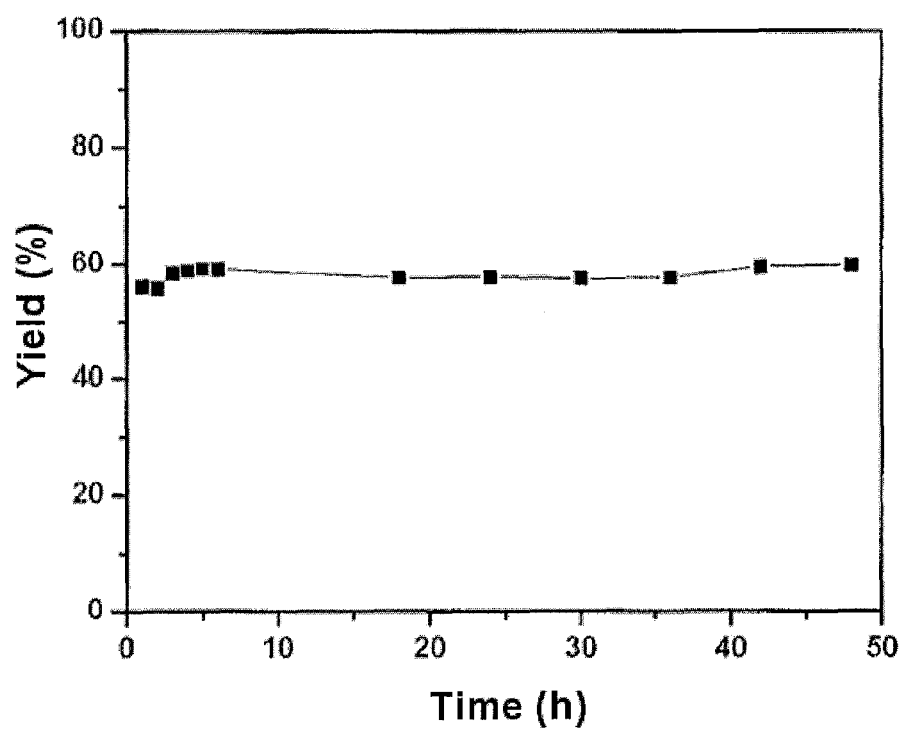
FIG. 2 is a graph showing the changes in the yield of 1,3-butadiene depending on the reaction time in the presence of the multicomponent bismuth molybdate catalyst coprecipitated from the coprecipitation solution at pH 8, according to an embodiment of the present invention.

In order to evaluate the degree of inactivation of the catalyst using the multicomponent bismuth molybdate catalyst prepared in Preparative Example 1 and obtained using the coprecipitation solution at pH 8, showing the highest catalytic activity in Experimental Example 1, oxidative dehydrogenation of the C4 mixture of Experimental Example 1 was conducted, and thus the yield of 1,3-butadiene depending on the reaction time was observed. The results are shown in FIG. 2. As shown in FIG. 2, almost no inactivation of the catalyst was observed for 48 hours after the initiation of the reaction, and high activity was continuously maintained. Thus, the catalyst prepared in the present invention can be seen to be very efficient for the oxidative dehydrogenation of n-butene.

The invention claimed is:

1. A method of preparing 1,3-butadiene, comprising:
   a) packing a multicomponent bismuth molybdate catalyst consisting of Bi, Ni, Fe and Mo as metal components in a fixed bed of a reactor;
   b) performing oxidative dehydrogenation while continuously passing a C4 raffinate-3 comprising n-butene and n-butane, air, and steam, as reactants, through a catalyst bed of the reactor, the C4 raffinate-3 containing at least 20 wt % of n-butane; and
   c) obtaining 1,3-butadiene, wherein the multicomponent bismuth molybdate catalyst is prepared by the following steps comprising:
   a) preparing a first solution containing a Ni precursor, a Fe precursor, and a Bi precursor;
   b) preparing a second solution in which a Mo precursor is dissolved;
   c) coprecipitating the precursors of Bi, Ni, Fe, and Mo by adding the first solution to the second solution to obtain a coprecipitation solution while adding a 1-3 M alkaline solution in droplets thereto such that a pH of the coprecipitation solution is adjusted to 7-8;
   d) stirring the coprecipitation solution having the adjusted pH for 1-2 hours, and removing water therefrom, thus obtaining a solid component; and
   e) drying the solid component at 20-300° C., and then performing thermal treatment at 400-600° C., and wherein a conversion of n-butene is equal or higher than 60.3%, a selectivity for 1,3-butadiene is equal or higher than 90.8% and a 1,3-butadiene yield is equal or higher than 54.9%.

2. The method according to claim 1, wherein a molar ratio of Ni precursor to Fe precursor to Bi precursor to Mo precursor is 1-10:1-5:1:5-20.3.

3. The method according to claim 1, wherein, in the a), the Ni precursor is nickel nitrate, the Fe precursor is iron nitrate, and the Bi precursor is bismuth nitrate.

4. The method according to claim 1, wherein the molybdenum precursor in the b) is ammonium molybdate.

5. The method according to claim 1, wherein the alkaline solution is an ammonia solution.

6. The method according to claim 1, wherein a volume ratio of n-butene to air to steam is 1:0.5~10:1~50.

7. The method according to claim 1, wherein the oxidative dehydrogenation is performed at a reaction temperature of 300~600° C. and at a gas hourly space velocity of 50~5000h$^{-1}$.

* * * * *